United States Patent
Ingenhoven et al.

(10) Patent No.: US 6,869,571 B2
(45) Date of Patent: Mar. 22, 2005

(54) DEVICE FOR ASPIRATING AND DISPENSING LIQUID SAMPLES

(75) Inventors: Nikolaus Ingenhoven, Mannedorf (CH); Noa Schmid, Grabs (CH); Stefano Fornito, Gossau (CH)

(73) Assignee: Tecan Trading AG, Mannedorf (CH)

( * ) Notice: Subject to any disclaimer, the term of this patent is extended or adjusted under 35 U.S.C. 154(b) by 518 days.

(21) Appl. No.: 09/993,252

(22) Filed: Nov. 19, 2001

(65) Prior Publication Data

US 2002/0131903 A1 Sep. 19, 2002

(30) Foreign Application Priority Data

Nov. 17, 2000 (CH) .............................. 2252/00
Nov. 29, 2000 (CH) .............................. 2314/00

(51) Int. Cl.[7] .................................. B01L 3/02
(52) U.S. Cl. .................. 422/100; 436/49; 436/180; 73/864.16; 73/864.17; 73/864.22
(58) Field of Search .......................... 422/100; 436/49, 436/180; 73/864.12, 864.16, 864.17, 864.22, 864.13

(56) References Cited

U.S. PATENT DOCUMENTS

| | | |
|---|---|---|
| 4,087,248 A | 5/1978 | Miles |
| 4,405,344 A | 9/1983 | Sisti et al. |
| 5,763,278 A | 6/1998 | Sickinger et al. |
| 5,916,524 A | 6/1999 | Tisone |
| 6,024,925 A | 2/2000 | Little et al. |

| | | | |
|---|---|---|---|
| 2001/0016358 A1 | * | 8/2001 | Osawa et al. ............... 436/180 |

FOREIGN PATENT DOCUMENTS

| | | |
|---|---|---|
| DE | 43 18 919 | 8/1994 |
| DE | 198 27 293 | 6/1999 |
| DE | 197 54 000 | 12/1999 |
| JP | 09 327628 | 12/1997 |
| WO | WO 97 15394 | 5/1997 |
| WO | WO 00/45955 | 8/2000 |

OTHER PUBLICATIONS

Schobert A et al."Accurate high–speed liquid handling of very small biological samples".Biotechniques vol. 15, No. 2 (1993).

* cited by examiner

Primary Examiner—Jan M. Ludlow
(74) Attorney, Agent, or Firm—McDonnell Boehnen Hulbert & Berghoff LLP

(57) ABSTRACT

A device (1) for aspirating and dispensing liquid samples having a pump (2), which comprises a cylindrical chamber (3), a piston (4) movable in this cylindrical chamber, and a piston drive (5) engaging on the piston. The device additionally comprises a pulse generator (6), which effects dispensing of samples from a liquid by generating pressure waves in this liquid and a tip (8) connected via a line (7) with the cylindrical chamber (3), with the piston drive (5) comprising a first drive (9) and a second drive (10), implemented as a pulse generator (6). Such a device comprises a channel (27) for rinsing or flushing the cylindrical chamber (3), with the channel (27) discharging into the cylindrical chamber (3). Furthermore, the invention also concerns systems with, for example, 384 or more such devices that are arranged in an array.

35 Claims, 2 Drawing Sheets

DEVICE FOR ASPIRATING AND DISPENSING LIQUID SAMPLES

This application claims priority under 35 U.S.C. §119 to Swiss patent application No. 2000 2252/00, filed Nov. 17, 2000 and Swiss patent application no. 2000 2314/00, filed Nov. 29, 2000.

FIELD OF THE INVENTION

The invention concerns devices for aspirating and dispensing liquid samples, as well as systems that include multiple devices of this type.

BACKGROUND OF THE INVENTION

It is known that droplets with a volume of more than 10 $\mu l$ can be dispensed from the air very easily, since if the pipette is correctly manipulated, the droplets leave the pipette tip of their own accord. The droplet size is then determined by the physical properties of the sample liquid, such as surface tension or viscosity. The droplet size thus limits the resolution of the quantity of liquid to be dispensed.

The aspirating and dispensing, i.e. the pipetting of liquid samples with a volume of less than 10 $\mu l$, in contrast, typically requires instruments and techniques which guarantee the dispensing of such small samples. The dispensing of a liquid with a pipette tip, i.e. with the endpiece of a device for aspirating and/or dispensing sample liquid, can occur from the air ("from air") or by touching a surface. This surface can be the solid surface of a container ("on tip touch"), into which the liquid sample is to be dispensed. It can also be the surface of a liquid in this container ("on liquid surface"). A mixing procedure following the dispensing is recommended, particularly for very small sample volumes in the nanoliter or even picoliter range, so that uniform distribution of the sample volume in a diluent is ensured.

Disposable tips significantly reduce the danger of unintentional transfer of parts of the sample (contamination). Simple disposable tips are known (so-called "air-displacement tips"), whose geometry and material is optimized for the exact aspirating and dispensing of very small volumes. The use of so-called "positive-displacement tips", which have a pump plunger inside, is also known.

For automation of the pipetting process, two procedures must be differentiated from one another: the defined aspiration and the subsequent dispensing of liquid samples. Between these procedures, typically the pipette tip is moved by the experimenter or by a robot, so that the aspiration location of a liquid sample is different from its dispensing location. For precision of aspiration and dispensing, only the liquid system is essential, which includes a pump (e.g. a diluter implemented as a syringe pump), tubing, and an endpiece (pipette tip). Among the many possible pumps for highly precise aspirating and dispensing of liquids, commercially available devices with the name "CAVRO XL 3000 Modular Digital Pump" or "CAVRO XP3000 plus Modular Digital Pump", sold by the firm Cavro Scientific Instruments Inc., Sunnyvale, Calif. USA, are available and perform suitably. Such pumps typically include a cylinder with a piston movable therein and a stepping motor for driving the piston. The stepping motor operates at a voltage of 24 V and is controlled by an external computer or microprocessor. Further details can, for example, be found in the "Operators Manual P/N 724043C" from Cavro Scientific Instruments Inc.

A device and a corresponding method for dispensing volumes are known from U.S. Pat. No. 5,763,278. This reference discloses automatic pipetting of small volumes, having a device including a pipetting needle, a diluter with a liquid outlet having a syringe, and a valve. The syringe includes a piston and a piston drive. A line connects the needle and the liquid outlet of the diluter, with the diluter and the line containing an essentially incompressible liquid. A pulse generator is located in the device and connected with the incompressible liquid in the line so that mechanical pulses with a force of at least 0.01 Ns can be output directly into the liquid of the line. A pulse of this type serves for driving the liquid out of the needle. The droplet size is defined by a targeted advance of the diluter piston and the droplet is ejected from the needle with a pulse. By defining the volume with the diluter, the droplet size and the reproducibility thereof depends on and is limited by the resolution of the diluter.

A pipetting device of this type that includes a piston pump and a pulse generator in the form of a piezoelectric element is disclosed in Japanese patent application JP 09 327628. The piezoelectric element is also the front plate of the piston and is used for terminating the dispensing procedure. The piston effects the majority of the liquid dispensing by its downward movement and is blocked during the actuation of the piezoelectric plate. The movement direction of the piezoelectric plate corresponds in this case to that of the piston. At least a part of the volume dispensed thus always depends on the movement of the piston, so that the reproducibility of the piston movement limits the resolution of the pipetting device.

SUMMARY OF THE INVENTION

An object of the present invention is to provide devices for aspirating and dispensing liquid samples as low as the picoliter volumetric range, in which the size of the droplets dispensed and the reproducibility thereof does not depend on the resolution of the diluter.

BRIEF DESCRIPTION OF THE DRAWINGS

The invention is illustrated by the drawings as disclosed herein. The invention will now be described in more detail with reference to schematic drawings, which illustrate preferred exemplary embodiments and are not to restrict the extent of the invention. As depicted herein, corresponding components have the same reference numbers in the figures.

DETAILED DESCRIPTION OF THE INVENTION

Figure 1:
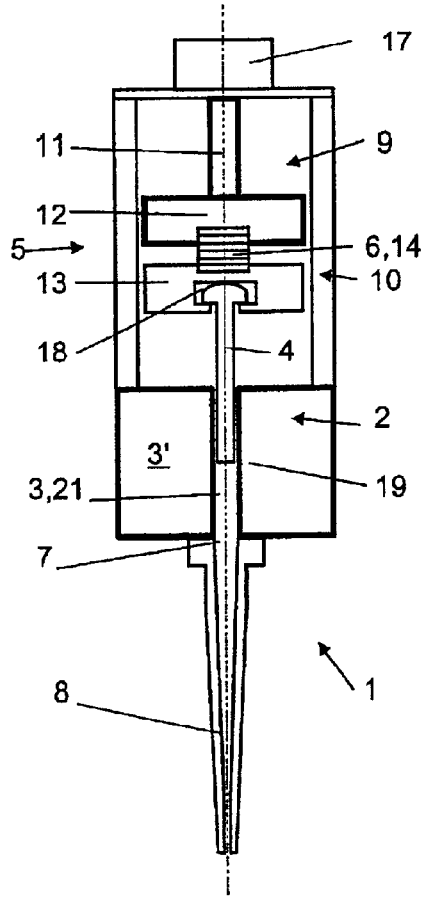
FIG. 1 shows a vertical section through a simple device for aspirating and dispensing liquid samples.

FIG. 1 shows a device 1 for aspirating and dispensing liquid samples having a pump 2. This pump comprises a cylindrical chamber 3, which in turn comprises a piston 4 movable in this cylinder and a piston drive 5 that engages the piston. In addition, the device 1 comprises a pulse generator 6, which generates pressure waves in the liquid as it is actuated to effect dispensing of samples from a liquid. An endpiece or a tip 8 is connected with the cylindrical chamber 3 via a line 7. This tip 8 is shown in the Figure as a steel needle that attaches directly to the body or on the cylinder block 3' of the pump 2. The tip 8 in embodiments as a steel needle preferably adjoins the cylindrical chamber 3 of the pump 2 without a transition, so that the steel pipette tip represents a continuous narrowing of the pump cylindrical chamber 3. This design prevents the occurrence of undesired eddies and allows the unimpeded expansion of the pressure waves triggered by the pulse generator 6 in the liquid to be pipetted.

The piston drive 5 comprises a first drive 9 and a second drive 10 implemented as a pulse generator 6. This first drive 9 is preferably implemented as a rotary spindle drive and comprises a spindle 11 and a first plate 12 movable with this spindle. The second drive 10 comprises a second plate 13 which is connected via a pulse generator 6 with the first plate 12 and which engages on the piston 4.

The space defined by cylindrical chamber 3 and piston 4, line 7, and tip 8 is preferably filled with a coherent liquid column, so that the volume of a liquid sample dispensed is defined, for a given tip geometry, solely by the parameters of a single pulse generated by the pulse generator 6. The cylindrical chamber 3 preferably contains 5 to 200 $\mu$l and the pulse generator 6 is embodied in this instance as a preloaded stack of piezoelectric elements 14. Additional results show that pipetting can also be done with an air bubble and/or an "air gap" in the line 7.

Notwithstanding the illustration in FIG. 1, the tip 8 for pipetting liquids can be embodied as a needle made of materials other than steel, or as a disposable plastic tip. Generally, the transition from the cylindrical chamber 3 to the tip 8 is then preferably produced with a so-called tip adapter 8'. Such a tip adapter is preferably produced from stainless-steel and is molded and outfitted in such a way that a secure and tight seat for a needle or disposable tip, produced, for example, from plastic, is ensured. The use of an O-ring between tip adapter 8' and tip 8 can favorably reinforce this seat and the required impermeability.

The specific arrangement of pump 2, piston drive 5, pulse generator 6, and tip 8 allows an extremely slender construction of the device 1, so that it is especially suitable for forming a component in a system for aspirating and dispensing liquid samples which comprise multiple devices 1 of this type. Such a system is, for example, a pipettor or (in the case of a system for dispensing samples) a dispenser. Such a system is preferably used for dispensing liquid into the wells of standard microplates with, for example, 96 wells (dispensing) or for aspirating liquids from one microplate and dispensing the samples in another microplate (pipetting). The reduction of the sample volumes (e.g. for filling high-density microplates having 384, 864, 1536, or even more wells) plays an increasingly important role, with the precision of the sample volume dispensed being assigned great importance. The time used for the dispensing and/or transferring of samples in this many wells is also significant. It is clear that multiple pipette tips that can be operated in parallel reduce the time used for the effective sample dispensing and/or for transferring by the same factor.

In principle, the invention thus provides a system having n devices, or at least such a system having n pumps 2, n lines 7, and n tips 8, having a first drive 9 and a second drive 10 and having m pulse generators which only needs 1/n of the dispensing time of a single device equipped with one of each of these components. The time factor thus plays a significant role during the filling of high-density microplates. These considerations are particularly significant if n is a multiple of 4—particularly 8, 96, or 384—and m is a whole number—particularly 1, 2, or 3.

Figure 2:
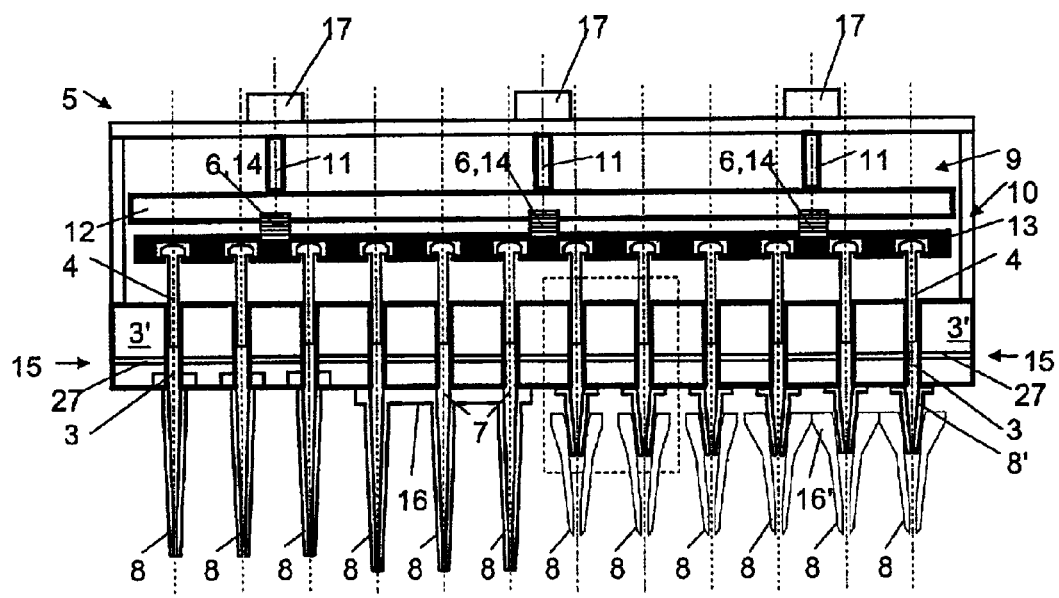
FIG. 2 shows a vertical section through a system for aspirating and dispensing liquid samples with an array of pumps and endpieces and/or tips arranged parallel to one another.

Because the arrangement of the wells in the microplates corresponds to a two-dimensional array, the components of a system such as pump 2, piston drive 5, pulse generator 6, and tip 8 are preferably arranged in the same way. In order to achieve compact construction, the pumps 2 and tips 8 are arranged parallel to one another at the same time. An example of such an arrangement is shown in FIG. 2.

The need for rapid pipettors in the life science fields has driven the development of multichannel pipettors. In prior art devices, both the number of the channels and/or the tips and the ranges of the sample volumes to be pipetted vary. Approximately 1 $\mu$l can be assumed as the practical volume limit for free dispensing from the air in this case.

Multichannel systems in which 4, 8, or 12 pipetting channels are distributed on one line have been known for some time. The tips are either arranged in a fixed raster (e.g. the MiniPrep device series from the firm CAVRO Scientific Instruments Inc., Sunnyvale, Calif., USA) or they can be spread out along one line (e.g. the GENESIS device series from TECAN Schweiz AG, Seestrasse 103, CH-8708 M ännedorf). The pipetting channels are either operated jointly via a stepping motor with one or more syringes or individually operated via the same number of diluters as syringes.

Multichannel systems for volumes in the sub-microliter range are known in the form of fixed two-dimensional combs (e.g. the PixSys4500 from Cartesian Technologies, Inc., 17851 Sky Park Circle, Irvine, Calif. 92614, USA) or from EP 0 956 449. These two-dimensional combs of pipettes, however, are typically no longer sufficient for the current demands for sample throughput.

Multichannel pipettors arranged in three dimensions are also known. They can be implemented as 96 tip devices with 96 individual hoses and 96 individual syringes, which are each driven in groups of 8 by a joint stepping motor (e.g. the MICROLAB MPH-96 Workstation from Hamilton Bonaduz AG, P.O. Box 26, 7402 Bonaduz, Switzerland). This system is very costly due to the large number of syringes and motors. In addition, it is difficult to remove interfering air bubbles from all of the hoses.

Arrays with up to 384 individual glass syringes with cannulas have also been arranged in the raster of a 384 microplate. The plungers of the syringes are moved simultaneously by one single stepping motor (e.g. the Hydra from Robbins Scientific, 1250 Elko Drive, Sunnyvale, Calif. 94089-2213, USA). The method is costly due to the many syringes. It cannot be expanded for disposable tips.

In place of diluters, syringes, and pistons, metal bellows have also been used (see U.S. Pat. No. 5,638,986, incorporated by reference). Due to the smaller mass to be moved, dispensing speeds are achieved that are suitable for dispensing volumes down to 0.5 $\mu$l from the air (e.g. the Liliput Dispenser from Fluilogic Systems Oy, Luoteisrinne 4, 02270 Espoo, Finland). A disadvantage is, however, that the metal bellows cannot be calibrated for example like a diluter.

The most frequently-used engineering principal for constructing three-dimensionally arranged multichannel pipettors comprises a plate to which or in which the 96 or 384 pistons or plungers are attached. This plate is moved, with the pistons for aspirating and/or dispensing, up and down by one or more motors.

The general disadvantage of all these systems (with the exception of the metal bellows) is that volumes in the sub-microliter range can only be dispensed "on tip touch" or "on liquid surface", but not without contact, directly from the air. A multichannel system according to the present invention, in contrast, allows the pipettable volume to be reduced down to the nanoliter range.

FIG. 2 shows a vertical section through a system provided by this invention for aspirating and dispensing liquid samples having an array of pumps 2 and tips 8 arranged in parallel to one another. The example shown symbolizes an array of 12×8, i.e. 96, pumps 2 and tips 8. This array corresponds to the format and layout of a microplate with 96 wells. Each component of this system comprises a device 1 for aspirating and dispensing liquid samples having a pump 2, which comprises a cylindrical chamber 3, a piston 4 movable in this cylinder, and a piston drive 5 engaging on the piston, having a pulse generator 6, that effects sample dispensing from a liquid by generating pressure waves in this liquid, and having a tip 8 connected via a line 7 with the cylindrical chamber 3, with the piston drive 5 comprising a first drive 9 and a second drive 10 implemented as a pulse generator 6. Each cylindrical chamber 3 preferably contains 5 to 200 μl, with the exact range depending on the layout, which can be adjusted depending on use. These devices are characterized in that they comprise a channel 27 for flushing or rinsing the cylindrical chamber 3, with the channel 27 discharging into the cylindrical chamber 3. One such drive 9, 10 can be provided per pipetting channel, but individual parts of the drive 9, 10 can be simplified or combined in subassemblies.

The entire matrix of the 96 pistons 4 is moved by three spindles 11. In this case, these three spindles act on the first plate 12 and, via the three piezoelectric stacks 14, on the second plate 13, which in turn acts on the pistons 4 in the cylinders. The spindles 11 are each driven by one precision motor 17, so that a first drive 9 comprises three simultaneously rotating spindles 11, which act on a joint first plate 12. The first drive 9 serves for moving the pistons 4 during aspiration of liquids and for supplying liquid in the tips 8 during and/or after the dispensing of liquid samples from the tips.

The second drive 10 comprises, in this case, three pulse generators 6, each having a preloaded stack of piezoelectric elements 14, which connect the first plate 12 with the second plate 13. The two plates 12, 13 are preferably permanently connected with one another via the piezo-electric stacks in such a way that they can be moved toward and away from one another without oscillation by these piezoelectric actuators. An actuation of the piezoelectric stacks moves the second plate 13, and thus also the pistons 4, preferably by up to 20 μm. The second plate 13 simultaneously engages on all 96 pistons 4. For this purpose, the second plate 13 has recesses 18 in which the free ends 19 of the pistons 4 engage and/or in which these ends 19 are held. The 96 pistons 4 are components of an array of 96 pumps arranged in parallel to one another. The cylinders are implemented as borings 21 in a cylinder block 3', in each of which one piston 4 is movably arranged. 96 lines 7 and/or 96 tips 8 are connected to the cylinder chambers 3.

The endpieces and/or tips 8 can be implemented singly, i.e. individually for each channel (as described under FIG. 1) or as tip plates 16, 16' having a corresponding number of, in this case, 96 tips 8. In FIG. 2, four examples (from left to right) of tips 8 are shown, in this case the first three are shown as single steel tips 8, the second three as a steel tip plate 16, the third three as single disposable tips 8, and the fourth three as a disposable tip plate 16'. Preferably, seals (not shown) are located between each of the tips 8 and their adapters 8' so that a secure seating of the tips 8 on their respective adapter 8' and/or the impermeability of the line 7 between piston 4 and pipette tip 8 is guaranteed.

Figure 3:
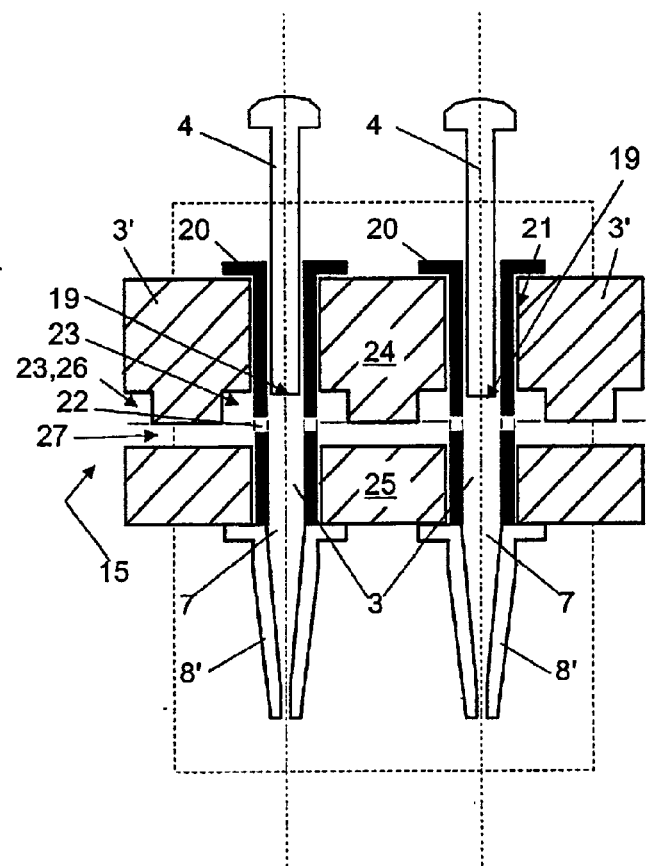
FIG. 3 shows an enlarged detail from FIG. 2, corresponding to the field indicated there.

In order that air bubbles can be prevented in or removed from the liquid which fills the cylindrical chambers 3, the lines 7, and the tips 8, a channel system 15 is provided for rinsing or flushing the cylindrical chambers 3 in the cylinder block 3'. Via a line (not shown), the entire channel system 15 and all cylindrical chambers 3 can thus be filled with liquid from the rear (not through the pipette tips 8) and thus be rinsed or flushed. The discharge of this channel system 15 in the region of the cylindrical chambers 3 is illustrated in FIG. 3. The cylindrical chambers 3 are identical in this exemplary embodiment with the inside of sleeves 20 which are inserted in borings 21 of the cylinder block 3'. Alternatively, the borings 21 in the cylinder block 3' can be used directly as cylinders (cf. FIG. 2). Alternatively to the channel system 15 having single channels 27 shown in FIG. 3, the supply of the pumps 2 can occur via a simpler channel system 15 (cf. FIG. 2). This extends essentially over the entire surface of the plates 12, 13 at approximately the same height and represents a simple, coherent cavity.

If sleeves 20 are used, these have a lateral, particularly continuous opening 22, which communicates with the channel system 15. In order that the individual rotational position of the sleeves 20 does not have any influence on the connection by the channel system 15, the channel system has an enlargement 23 in the region of each sleeve 20. In this case, the cylinder block 3' is preferably produced in two parts. In this case, circular depressions 26 are located in a first part 24 of the cylinder block 3' and the single channels 27 of the channel system 15 are located in a second part 25 of the cylinder block 3'. Depending on the material (glass, steel, plastic etc.), which is selected for the parts of the cylinder block 3', this can be performed with embedding, milling, etching, or other suitable methods. An injection molded part 24, 25 made of plastic can also have such channels 27.

Alternatively to this embodiment, depressions 26 and single channels 27 can also be molded into one part of the cylinder block 3' and the other part of the cylinder block 3' can be implemented as a plate. Not-withstanding the illustration in FIG. 3, the lower end of the sleeves 20 can be directly implemented as a tip adapter 8'. In addition, actuation, i.e. the pressure wave generation, deviating from the use of one or more piezoelectric stacks, can be produced, for example, by a pneumatic, magnetic, or thermal pulse generator. As another alternative to the embodiment shown, the first and/or the second plate (12, 13) can have a shape deviating from a rectangle and, for example, have a square, hexagonal, octagonal, oval, or even round shape.

A pulse is output from the pulse generator 6 implemented as a piezo-electric stack 14 onto the second plate 13. This plate 13 relays the impact to the individual pistons 4, which perform a correspondingly short and targeted movement in their cylindrical chambers 3. This movement triggers a pressure wave in the liquid in each cylindrical chamber 3 simultaneously. The position of the pistons 4 within the cylindrical chamber 3 is preferably selected for this triggering of pressure waves (deviating from the illustration in FIG. 3) in such a way that the free piston ends 19 come to rest between the openings 22 and the line 7. In this way, the openings 22 are sealed by the pistons 4 and the pressure waves can expand in the liquid only to the pipette tips 8, as desired. The openings 22 preferably have as large an area as possible and the single channels 27 have a large inner diameter, in order that the wash or flush liquid experiences the least possible flow resistance.

Deviating from these illustrations in FIGS. 2 and 3, for example, 4 or 8 and/or even 16 or more pumps 2 and tips 8 can be arranged in a linear array which is made up of one single row. Preferably, however, 96, 384, or more pumps 2 and tips 8 are arranged in parallel in a two-dimensional array in such a way that this array corresponds to the format and the layout of a microplate with 96, 384, 864, 1536, or more wells. Such an array of pumps 2 and tips 8, each arranged parallel to one another, allows the simultaneous aspiration or dispensing of 96, 384, or more samples, which allows the time for processing of a corresponding high-density microplate to be significantly reduced.

Figure 4:
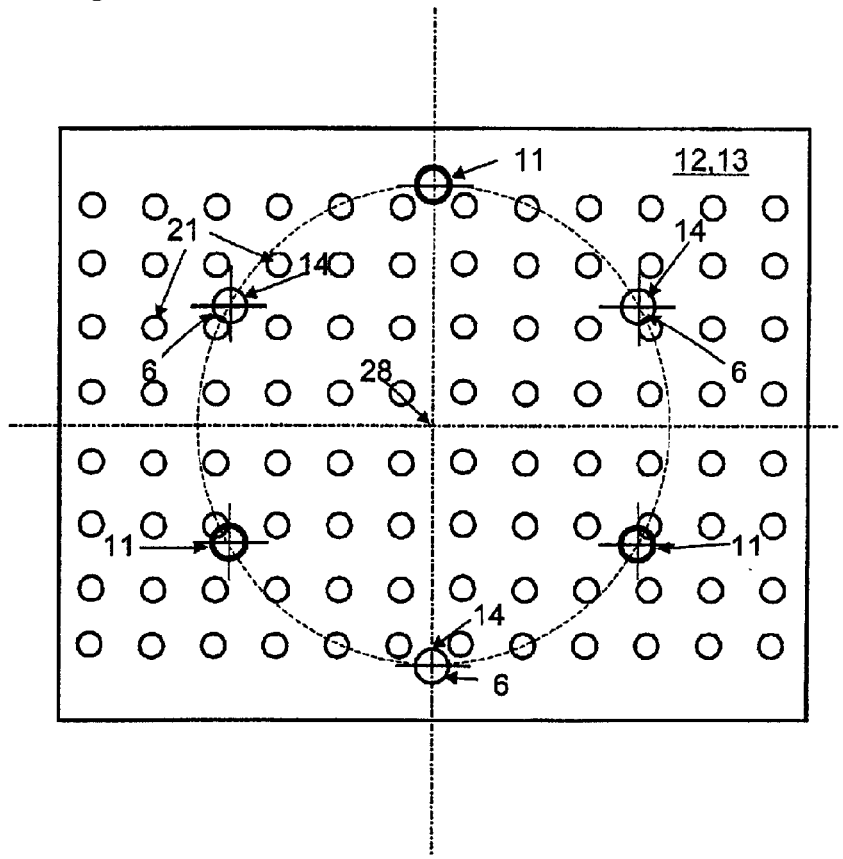
FIG. 4 shows a horizontal projection of a lay out of the piston drive according t o a first embodiment.

FIG. 4 shows, in a horizontal projection, a layout of the piston drive 5 according to a first embodiment. Three spindles 11 and three pulse generators 6 are each positioned at the same distance from the center of the cylinder block 3' and/or the two plates 12, 13, with this same distance also lying between them and the nearest pulse generator 6 and/or spindle 11. A trigonal symmetry whose center 28 lies in the center of the cylinder block 3' and/or the two plates 12, 13 results from this. This symmetry allows uniform distribution of the forces in the plates 12, 13 and thus uniform displacement of the plates with the first drive 9 and the second drive 10. In this case as well, the liquid is fed into the tip with the first drive, so that before each pulse by the second drive, a coherent liquid column fills up the active space of cylindrical space 3, line 7, and tip 8. The layout described has the advantage that the levels of the plates 12, 13 are never redundant and that only three piezoelectric stacks are sufficient to dispense 96 or even 384 or more samples simultaneously.

Figure 5:
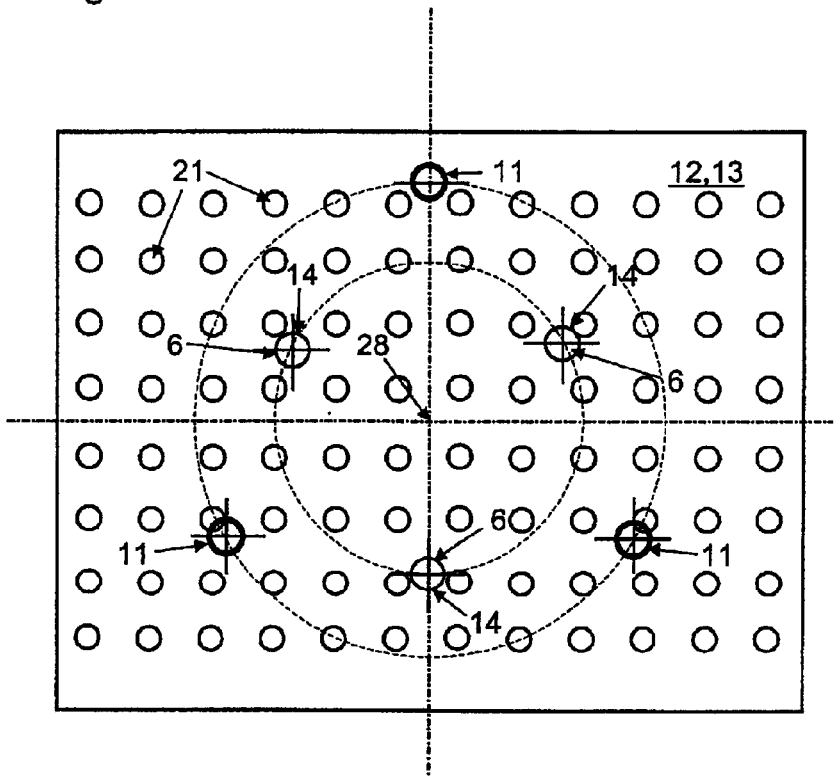
FIG. 5 shows a horizontal projection of a layout of the piston drive according to a second embodiment.

FIG. 5 shows a horizontal projection of a layout of the piston drive according to a second embodiment. In contrast to FIG. 4, in this case the spindles 11 and the pulse generators 6 are not located on a common graduated circle (indicated with dashed lines). However, the spindles 11 and/or the pulse generators 6 each define a triangle, whose center of gravity always corresponds with the center of symmetry 28, in both FIG. 4 and in FIG. 5. The symmetry achieved in this way allows uniform distribution of the forces in the plates 12, 13 and therefore uniform displacement of these plates with the first drive 9 and the second drive 10. Further arrangements that correspond to this symmetry principle are included in the extent of this invention.

In practice, a further variant of an arrangement of the pulse generators 6 has proven itself in which the piezoelectric stacks 14 are positioned in the corners of an equilateral triangle and the base of this triangle runs essentially parallel to a longitudinal edge of the plates 12, 13 and measures approximately ⅓ of its length. The center of gravity of this triangle again lies in the center of symmetry 28 of the plates 12, 13.

For pipetting from, for example, a 96 well microplate, if disposable tips are used, first these are picked up. The plates 12, 13 are pulled back with the first drive 9 far enough that the ends 19 of the pistons 4 come to rest behind the openings 22 in the sleeves 20. The channels 27, the cylindrical chambers 3, the lines 7, and/or the tips 8 and tip adapters 8' are then rinsed or flushed and/or filled with system liquid (e.g. with deionized or distilled water). Subsequently, the pistons 4 are moved in the direction of the tips 8 in order to prepare the pumps 2 to aspirate liquid via the tips. If the pistons 4 are moved to their forwardmost position in this case, a maximum aspiration capacity is made available. After the array having 96 pumps 2 and tips 8 is moved over the liquid to be aspirated, the tips are dipped somewhat into the liquid. By pulling back the pistons 4 with the first drive 9, with the path being determined by the rotation of the spindles 11, the aspiration of the liquid to be pipetted occurs, and does so simultaneously in all tips 8.

For dispensing, the pistons 4 are moved toward the tips 8. In order for the liquid to break away cleanly from the tips 8 and therefore to produce exact volumes, a specific minimum speed and abrupt stopping of the pistons 4 at the end of dispensing is necessary. For volumes to be dispensed that are in the microliter range, the first drive 9 is typically sufficient for precise sample dispensing. In the sub-microliter range, in contrast, acceleration and abrupt stopping of the spindle drive is no longer sufficient to ensure that the liquid to be dispensed breaks away cleanly. For this reason, the pistons 4 are additionally moved with the second drive 10 by piezoelectric actuation.

This actuation occurs through appropriate electrical rectangular pulses output with a frequency of 1 to 1000 Hz at the piezoelectric stacks 14, which are performed simultaneously with the movement of the piston matrix and, together with this movement, determine the volume of the samples to be dispensed. These movements of the two drives 9, 10 are preferably synchronized in such a way that the first pulse occurs with the beginning of the travel of the pistons 4 and the last pulse with the end of this travel. Due to this synchronization, the piezoelectric actuation ensures that the droplets break away cleanly, even if the piston matrix moves slowly. This is made possible, as described, by transmission of the pulses triggered by the pulse generator 6 and transferred with the second plate 13 onto the pistons 4 and thus onto the liquid in the cylindrical chambers 3.

For dispensing in the range of a few nl, the single droplet volume can also be determined solely by the strength of the piezoelectric actuation. The total volume dispensed is thus a product of the number of droplets and their content. The single droplet size is determined in this type of dispensing primarily by the strength of actuation and by the diameter of the opening of the pipette tip 8. These two parameters are then also preferably adjusted to the quantity and the physicochemical properties of the liquid to be pipetted.

Four operating modes result from the aforementioned:

A    Large volumes

The dispensing of volumes of more than one microliter is performed by advancing the pistons 4 and is determined solely by the first drive 9, implemented as a spindle drive.

B    Medium volumes

The dispensing of droplets between 0.5 and 1 µl is performed by advancing the pistons 4 and is determined by the first drive 9, implemented as a spindle drive. The additional piezoelectric actuation allows the droplets to break away cleanly. Furthermore, the following variants are possible:

B1   After the piston 4 is advanced, the piezoelectric stack is actuated once in order to ensure clean droplet breakaway from the air.

B2   Before the piston 4 is displaced, the piezoelectric stack is actuated once in order to generate a defined breakaway edge in the tip. The volume is defined by the advance of the piston 4 and the piezoelectric actuation allows droplet breakaway at the same position.

B3   The piezoelectric actuator is activated during the entire advance of the piston 4 and the liquid stream is "chopped" into single droplets. The volume is defined by the advance.

C    Small volumes

The dispensing of droplets of less than 0.5 µl is performed by the second drive 10, implemented as a piezoelectric actuator. The -continued advancing of the pistons 4 with the first drive 9, implemented as a spindle drive, serves for compensating for the volumes dispensed. Ideally, the compensation occurs in such a way that the space defined by cylindrical chamber 3, piston 4, line 7, and tip 8 is completely filled with a coherent liquid column at least before the next pulse output. Therefore, when the system according to the invention is used, the volume of a liquid sample dispensed is defined, for a given tip geometry, solely by the parameters of one single pulse generated by the pulse generator 6.

D  Very small volumes

If the liquid column is pulled back slightly from the tip opening, it becomes possible to eject single droplets of up to 10 nl out of a tip opening of up to 500 μm in diameter with single pulses of the piezoelectric actuator. The droplet volume is therefore only dependent on the pulse strength, but not on the diameter of the opening.

All of the pipetting modes described above can be used either with or without an air bubble ("separation air gap") for separating samples and system liquid. Also, both fixed tips and disposable plastic tips can be used.

Without the separation air gap, pipetting can be performed somewhat more precisely than with an air gap, but the sample is somewhat diluted by the system liquid, which causes somewhat more sample material to be aspirated than is dispensed. The slightly diluted residue is discarded.

A great advantage of the devices and systems according to the invention is that, with one single device, large, medium, and small sample volumes can be dispensed with high precision and with practically any desired number of channels (single pipettes up to arrays with 384 and more pipettes).

The diameter of the opening of the pipette tip 8 is, depending on the volume range desired of the samples to be dispensed, 25 μm to 500 μm. The inner diameter of the pipette tips and/or the needles tapers from approximately 0.5 mm to 1 mm toward the outlet of the tip 8. The faces of the tips 8 are to be as small as possible within the framework of production capabilities.

The devices 1 and systems according to the invention preferably comprise a computer—e.g. integrated or also provided—for synchronizing the two drives 9, 10 and/or for controlling the aspiration and dispensing of liquid samples.

What is claimed is:

1. A device for aspirating and dispensing liquid samples comprising a pump that comprises a cylindrical chamber, a piston movable in this cylindrical chamber and a piston drive that engages the piston, the device further comprising a pulse generator that effects dispensing of samples from a liquid by generating pressure waves in this liquid, and a tip connected to the cylindrical chamber with a line, wherein the piston drive comprises a first drive and a second drive used as the pulse generator, and wherein the device also comprises a channel for flushing or rinsing the cylindrical chamber, and the channel discharges into the cylindrical chamber.

2. The device according to claim 1, wherein the cylindrical chamber, piston, line, and tip define a space therebetween that is filled with an essentially coherent liquid column in the presence or absence of an air gap, and the volume of a liquid sample dispensed is determined solely by the parameters of one single pulse generated by the pulse generator.

3. The device according to claim 1, wherein the first drive comprises a first plate movable with a spindle connected thereto and the second drive comprises a second plate connected with the first plate by the pulse generator and engages the piston.

4. The device according to claim 2, wherein the first drive comprises a first plate movable with a spindle connected thereto and the second drive comprises a second plate connected with the first plate by the pulse generator and engages the piston.

5. A device according to claim 1, 2, 3 or 4, wherein the cylindrical chamber has a volume of between 5 and 200 μl.

6. A device according to claim 1, 2, 3 or 4, wherein the pulse generator comprises a reloaded stack of piezoelectric elements.

7. A device according to claim 1, 2, 3 or 4, wherein the tip is a disposable tip or needle for pipetting liquids.

8. A system for aspirating and dispensing liquid samples, comprising a plurality of devices according to claims 1, 2, 3 or 4.

9. A system for aspirating and dispensing liquid samples, comprising a plurality of devices according to claim 5.

10. A system for aspirating and dispensing liquid samples, comprising a plurality of devices according to claim 6.

11. A system for aspirating and dispensing liquid samples, comprising a plurality of devices according to claim 7.

12. A system according to claim 8 comprising n pumps, n lines, and n tips, the first drive and the second drive having m pulse generators, wherein n is a whole number selected from 8, 96, or 384 and m is a whole number selected from 1, 2, or 3.

13. A system according to claim 9 comprising n pumps, n lines, and n tips, the first drive and the second drive having m pulse generators, wherein n is a whole number selected from 8, 96, or 384 and m is a whole number selected from 1, 2, or 3.

14. A system according to claim 12, comprising an array of pumps and tips arranged in parallel to one another, wherein the array corresponds in layout and format of a microplate having 96, 384, 864, 1536, or more wells.

15. A system according to claim 13, comprising an array of pumps and tips arranged in parallel to one another, wherein the array corresponds in layout and format of a microplate having 96, 384, 864, 1536, or more wells.

16. A system according to claim 8, comprising an array of 96, 384, or more pumps, lines, and tips, arranged in parallel to one another, the first drive, comprising at least three spindles acting on a joint first plate, and the second drive, comprising at least three pulse generators, each having a preloaded stack of piezoelectric elements, with the second drive additionally comprising a second plate connected to the first plate via the pulse generators and that engages all pistons simultaneously.

17. A system according claim 9, comprising an array of 96, 384, or more pumps, lines, and tips, arranged in parallel to one another, the first drive, comprising at least three spindles acting on a joint first plate, and the second drive, comprising at least three pulse generators, each having a preloaded stack of piezoelectric elements, with the second drive additionally comprising a second plate that is connected to the first plate by the pulse generators and that engage all pistons simultaneously.

18. A system according to claim 16, comprising a channel system that discharges into each of the cylindrical chambers.

19. A system according to claim 17, comprising a channel system that discharges into each of the cylindrical chambers.

20. A system according to claim 8, wherein the tips are tip plates (16, 16') that can be removed or automatically picked up and discarded.

21. A system according to claim 9, wherein the tips are tip plates (16, 16') that can be removed or automatically picked up and discarded.

22. A system according to claim 8, further comprising a computer for controlling the aspiration and dispensing of liquid samples.

23. A system according to claim 9, further comprising a computer for controlling the aspiration and dispensing of liquid samples.

24. A system according to claim 10 comprising n pumps, n lines, and n tips, the first drive and the second drive having m pulse generators, wherein n is a whole number selected from 8, 96, or 384 and m is a whole number selected from 1, 2, or 3.

25. A system according to claim 11 comprising n pumps, n lines, and n tips, the first drive and the second drive having m pulse generators, wherein n is a whole number selected from 8, 96, or 384 and m is a whole number selected from 1, 2, or 3.

26. A system according to claim 10, comprising an array of 96, 384, or more pumps, lines, and tips, arranged in parallel to one another, the first drive, comprising at least three spindles acting on a joint first plate, and the second drive, comprising at least three pulse generators, each having a preloaded stack of piezoelectric elements, with the second drive additionally comprising a second plate that is connected to the first plate by the pulse generators and that engage all pistons simultaneously.

27. A system according to claim 11, comprising an array of 96, 384, or more pumps, lines, and tips, arranged in parallel to one another, the first drive, comprising at least three spindles acting on a joint first plate, and the second drive, comprising at least three pulse generators, each having a preloaded stack of piezoelectric elements, with the second drive additionally comprising a second plate that is connected to the first plate by the pulse generators and that engage all pistons simultaneously.

28. A system according to claim 10, further comprising a computer for controlling the aspiration and dispensing of liquid samples.

29. A system according to claim 11, further comprising a computer for controlling the aspiration and dispensing of liquid samples.

30. A system according to claim 24, comprising an array of pumps and tips arranged in parallel to one another, wherein the array corresponds in layout and format of a microplate having 96, 384, 864, 1536, or more wells.

31. A system according to claim 25, comprising an array of pumps and tips arranged in parallel to one another, wherein the array corresponds in layout and format of a microplate having 96, 384, 864, 1536, or more wells.

32. A system according to claim 27, comprising a channel system that discharges into each of the cylindrical chambers.

33. A system according to claim 28, comprising a channel system that discharges into each of the cylindrical chambers.

34. A system according to claim 10, wherein the tips are tip plates (16, 16') that can be removed or automatically picked up and discarded.

35. A system according to claim 11, wherein the tips are tip plates (16, 16') that can be removed or automatically picked up and discarded.

* * * * *